(12) United States Patent
Rangheard et al.

(10) Patent No.: US 8,575,056 B2
(45) Date of Patent: *Nov. 5, 2013

(54) METHOD OF PREPARING A CATALYTIC COMPOSITION FOR DIMERIZATION, CO-DIMERIZATION AND OLIGOMERIZATION OF OLEFINS

(75) Inventors: Claudine Rangheard, Lyons (FR); Helene Olivier-Bourbigou, Sanit Genis-Laval (FR); Emmanuel Pellier, Tupin Semons (FR); David Proriol, Brignais (FR)

(73) Assignee: IFP Energies nouvelles, Rueil Malmaison Cedex (FR)

( * ) Notice: Subject to any disclaimer, the term of this patent is extended or adjusted under 35 U.S.C. 154(b) by 484 days.

This patent is subject to a terminal disclaimer.

(21) Appl. No.: 12/811,635

(22) PCT Filed: Dec. 10, 2008

(86) PCT No.: PCT/FR2008/001718
§ 371 (c)(1),
(2), (4) Date: Sep. 15, 2010

(87) PCT Pub. No.: WO2009/103877
PCT Pub. Date: Aug. 27, 2009

(65) Prior Publication Data
US 2011/0009581 A1     Jan. 13, 2011

(30) Foreign Application Priority Data

Jan. 4, 2008  (FR) ..................................... 08 00062

(51) Int. Cl.
*B01J 31/28*  (2006.01)
*B01J 31/00*  (2006.01)

(52) U.S. Cl.
USPC ........... 502/104; 502/102; 502/103; 526/172; 526/169.1

(58) Field of Classification Search
USPC ........... 556/138; 526/172, 161; 502/104, 102, 502/103
See application file for complete search history.

(56) References Cited

U.S. PATENT DOCUMENTS

| 6,730,788 | B1 | 5/2004 | Helquist | |
| 8,101,762 | B2* | 1/2012 | Rangheard et al. | 546/88 |
| 2011/0009581 | A1* | 1/2011 | Rangheard et al. | 526/172 |
| 2011/0263804 | A1* | 10/2011 | Rangheard et al. | 526/172 |

OTHER PUBLICATIONS

Rangheard, C.; Proriol, D.; Olivier-Bourbigou, H.; Braunstein, P. Dalton Trans., 2009, 770-772.*
Jie, S.; Zhang, S.; Sun, W.-H.; Kuang, X.; Liu, T.; Guo, J. J. Mol. Catal. A: Chemical, 2007, 269, 85-96.*
International Search Report of PCT/FR2008/001718 (Jul. 23, 2009).
R. Zong et al. "Synthetic Approaches to Polypyridyl Bridging Ligands with Proximal Multidentate Binding Sites", Journal of Organic Chemistry, vol. 71, No. 1 (2006) pp. 167-175.
C. Y. Hung et al., "A Friedländer Approach to Novel 1,10-Phenantrholines and Their Use as Ligands for Ru(II) and Cu(I)", Tetrahedron, vol. 50, No. 36 (1994) pp. 10685-10692.
E. C. Riesgo et al., "Introduction of Benzo[h]Quinoline and 1,10-Phenanthroline Subunits by Friedländer Methodology", Journal of Organic Chemistry, vol. 61, No. 9 (1996) pp. 3017-3022.
S. Jie et al., "Iron(II) Complexes Ligated by 2-Imino-1,10-Phenanthrolines : Preparation and Catalytic Behavior Toward Ethylene Oligomerization", Journal of Molecular Catalysis A, vol. 269, No. 1-2 (Apr. 3, 2007) pp. 85-96.
C. Rangheard et al., "Direct Synthesis of a New Class of N,N,N Ligands Based on 1,2-Dihydro-1,10-Phenanthroline Backbone and Their Coordination to Pd Complexes", Journal of the Chemical Society, No. 5 (Dec. 12, 2008) pp. 770-772.

* cited by examiner

*Primary Examiner* — Rip A. Lee
(74) *Attorney, Agent, or Firm* — Millen, White, Zelano & Branigan, P.C.

(57) ABSTRACT

The present invention describes a method of preparing a catalytic composition used for oligomerization, co-dimerization or polymerization of olefins, wherein the compound obtained upon contacting at least one iron compound with at least one nitrogen-containing compound is subjected to an oxidation stage prior to being mixed with an activating agent and optionally with a solvent.

The present invention also describes the catalytic composition obtained by means of said preparation method and the use thereof for oligomerization, co-dimerization or polymerization of olefins.

22 Claims, 4 Drawing Sheets

METHOD OF PREPARING A CATALYTIC COMPOSITION FOR DIMERIZATION, CO-DIMERIZATION AND OLIGOMERIZATION OF OLEFINS

CROSS-REFERENCE TO RELATED APPLICATION

This application is related to a concurrently filed application, Ser. No. 12/829,895 entitled "Novel Nitrogen-Containing Organic Compounds Usable As Catalytic Composition Precursors" by the same inventors and based on PCT/FR2008/001720 filed Dec. 10, 2008 and FR 08/00061 filed Jan. 4, 2008, incorporated by reference herein.

FIELD OF THE INVENTION

The present invention relates to a method of preparing a catalytic composition used for dimerization, co-dimerization, oligomerization or polymerization of olefins.

BACKGROUND OF THE INVENTION

There are various prospects for linear $\alpha$-olefins, notably those containing 4 to 20 carbon atoms, depending on the length of their carbon chain. For example, $C_4$ to $C_8$ olefins are mainly used as co-monomers for the production of low-density polyethylenes (LLDPE), $C_8$ to $C_{14}$ olefins as intermediates in the lubricant industry, and $C_{10}$-$C_{18}$ olefins for the production of detergents. These olefins experience a strong economic growth. Most industrial $\alpha$-olefin production processes are ethylene oligomerization methods catalyzed by transition metal complexes (Ni, Ti, Zr) or $AlEt_3$ (Alpha Olefins Applications Handbook, G. R. Lapin and J. D. Sauer Eds M. Dekker, NY, 1989). Most of these processes lead to Schulz-Flory type distributions, which can be quantified by value K. This value K represents the chain propagation probability and it is experimentally determined by the $C_{n+2}/C_n$ molar ratio. The values of K that are encountered in industrial processes are of the order of 0.7-0.8, which corresponds to wide $\alpha$-olefin distributions ranging from $C_4$ to $C_{20}^+$. It is then difficult to upgrade all of the products formed, in particular the "waxes" (olefins>C30).

On the other hand, not insignificant amounts of branched or internal olefins can also be produced by such methods, olefins that are often difficult to separate and unwanted for industrial processes. It is therefore important to develop new methods allowing these olefins to be minimized.

Incessant research work has been done during the past years in order to find new catalytic systems allowing to obtain narrower olefin distributions, for example allowing to optimize the formation of $C_4$-$C_{10}$, more selective in linear alpha-olefins and more active.

Relatively recently, catalytic systems comprising group 8-10 transition metals such as iron, nickel, palladium and cobalt associated with diimine type chelate ligands have been developed and applied for ethylene polymerization or copolymerization of alpha-olefins or olefins carrying a function, such as methyl acrylate (see for example the review by V. Gibson in Angew. Chem. Int. Ed. 1999, 38, 429). These systems most often use a co-catalyst that is an aluminium derivative such as an aluminoxane.

More recently, it has been shown (S. Svejda et al., Organometallics, 1999, 18, 65-74; WO-A-96/2310; WO-A-00/10, 945; and U.S. Pat. No. 5,880,323) that systems comprising a nickel complex associated with an $\alpha$-diimine type ligand in the presence of a Lewis acid or a Bronsted acid, more particularly an aluminium derivative such as an aluminoxane or an alkylaluminium chloride, allow to catalyze the oligomerization of ethylene to linear $\alpha$-olefins. However, in these systems, the amounts of aluminoxane used are generally high (more than 100 equivalents per mole of nickel) and the distribution of the olefins formed is wide: from C4 to C20, with a Schulz-Flory constant generally above 0.6.

It has also been shown that some iron complexes associated with bis(imino)pyridine type trident chelate ligands, activated by an aluminium alkyl derivative and more particularly an aluminoxane, catalyze the oligomerization of ethylene (see the review by V. Gibson, Chem. Rev. 2007, 107, 1745; Du Pont de Nemours WO99/02472; WO 02/06192 A1; Britovek et al, Chem. Eur. J., 2000, 6, 12, pp 2221-2231, BP Chemicals WO 99112981; Chevron Phillips WO2005/080301A 1).

The distribution of the oligomers formed essentially depends on the nature of the bis(imino)pyridine ligand, in particular the substituents on the aromatic rings of the imines. These distribution generally follow a Schulz-Flory type law whose characteristic factor K ranges from 0.70 to 0.85 (M. Brookhart, S. Brooke, J. Am. Chem. Soc. 1998, 120, 7143-7144).

Shell International Research (WO 01/58874 A1; WO 02/00339 A2, WO 2004/037415 A2; WO 2007/059015) teaches that the use of dissymmetric pyridine bis-arylimine ligands associated with iron complexes activated by an aluminoxane allows to obtain Schulz-Flory linear olefin distributions (no deviation) with a high minimization of the production of mass products.

Exxon Mobil describes, in patent application US-2005/0, 192,470, a method of producing linear $\alpha$-olefins whose chain length does not exceed 12 carbon atoms (short Schulz-Flory distribution, K=0.45) when using the 2,6-bis-phenylimine-pyridine ligand associated with a complex, preferably a Fe(II) complex, and an aluminoxane.

These complexes, which carry very weakly encumbered bis-aryliminie-pyridine ligands, lead to the shortest oligomer distributions. However, they involve the drawback of being poorly stable and they are rapidly deactivated, particularly with temperature.

Surprisingly enough, we have discovered that when the complexes resulting from the combination of a nitrogen-containing ligand obtained by reaction of a compound X with a compound Y, whose general formulas are described hereafter, with an iron compound are previously subjected to an oxidation stage, novel precursors of olefin oligomerization, co-dimerization or polymerization catalysts that do not involve the drawbacks of the aforementioned systems are obtained.

SUMMARY OF THE INVENTION

The present invention describes a method of preparing a catalytic composition used for olefin oligomerization, co-dimerization or polymerization, wherein at least one compound obtained upon contacting at least one iron compound with at least one nitrogen-containing ligand resulting from the reaction of compound X with compound Y is subjected to an oxidation stage prior to being mixed with an activating agent and optionally a solvent.

The present invention also describes the catalytic composition obtained by means of said method and the use thereof for olefin oligomerization, co-dimerization or polymerization.

DETAILED DESCRIPTION

Figure 1:
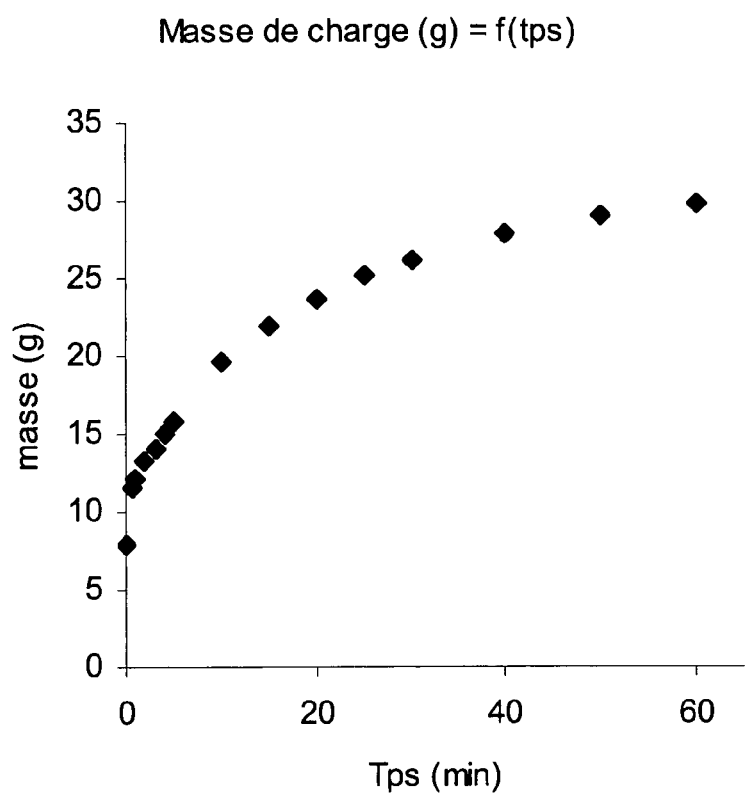
FIGS. 1 to 4 show the consumption in weight of ethylene measured as a function of time. This consumption is representative of the activity of the catalytic system during various catalytic tests respectively described according to Examples 9 (FIGS. 1 to 3) and 10 (FIG. 4).
Figure 2:
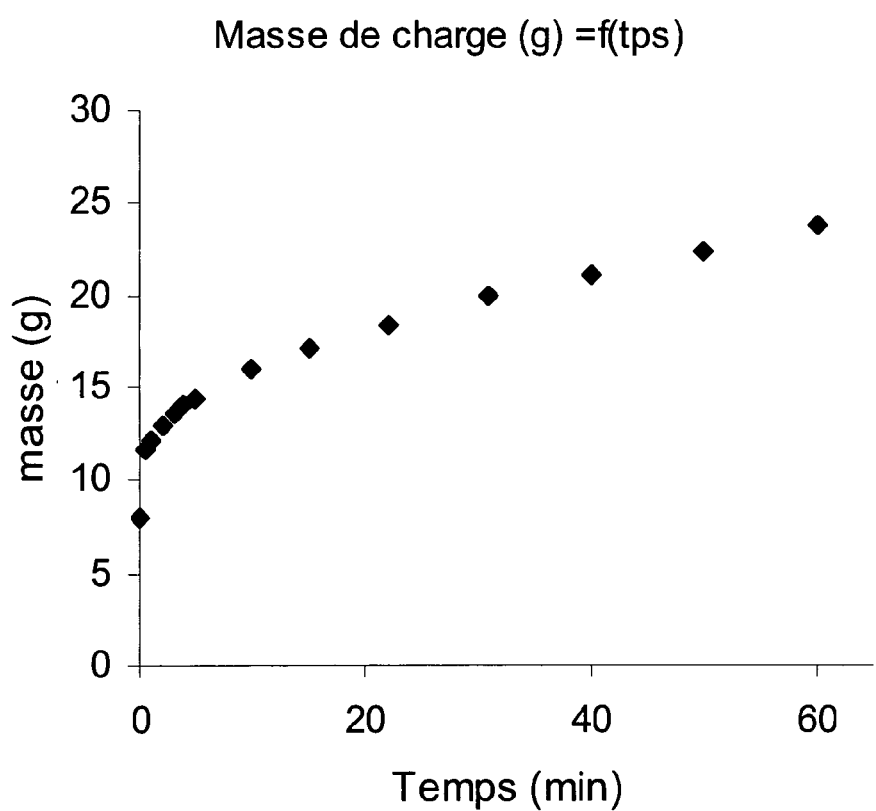
Figure 3:
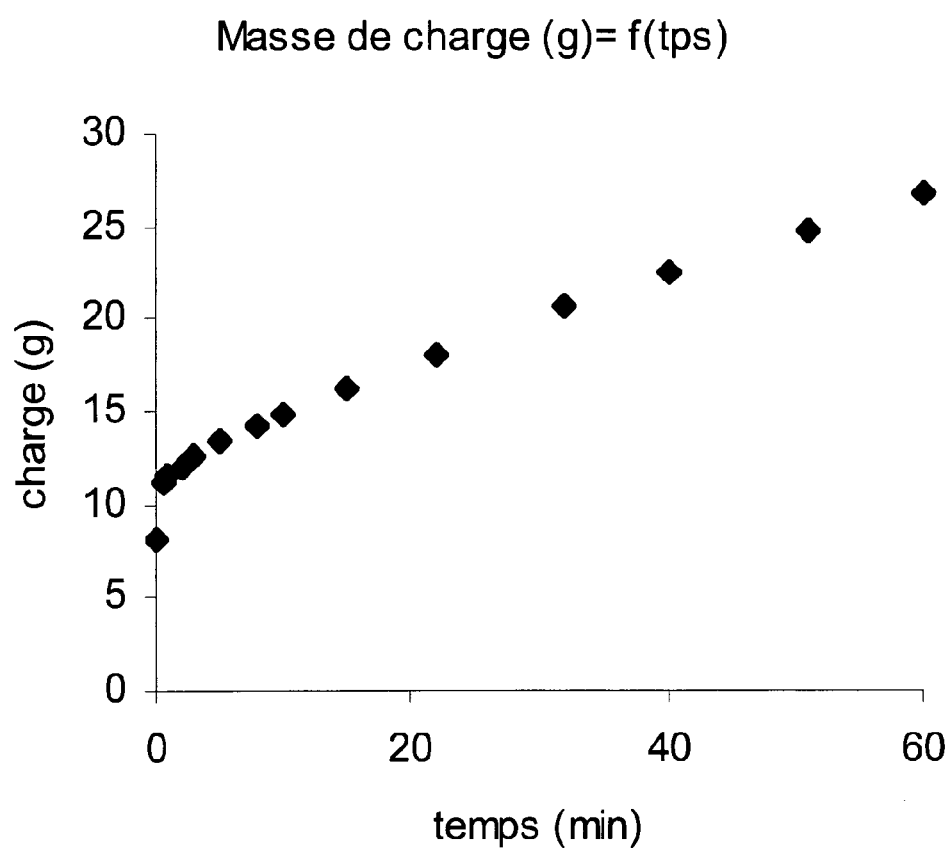

The present invention describes a method of preparing a catalytic composition comprising the following stages:

a) contacting, optionally in the presence of a solvent, at least one iron compound (compound A) with at least one compound B resulting from the condensation of a compound X with a compound Y whose general formulas are given below:

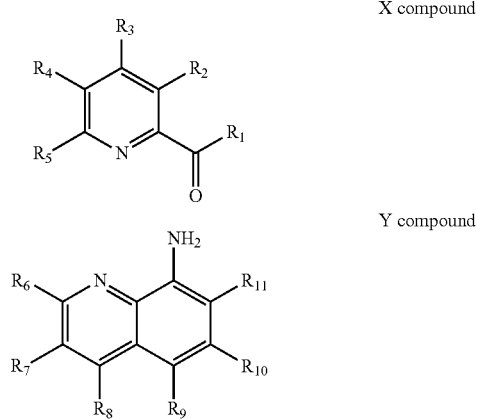

$R_1$ to $R_{11}$, identical or different, represent alkyl groups, saturated or not, cycloalkyl or aromatic, aryl or aralkyl, possibly substituted.

$R_1$ to $R_{11}$, identical or different, can also represent organic radicals wherein one or more hydrogen atoms are replaced by halogenides, a fluoride for example, or groups comprising at least one heteroelement such as oxygen, nitrogen, sulfur, phosphorus or silicon. These heteroelements can be contained in saturated or unsaturated or aromatic alkyl rings.

$R_1$ to $R_{11}$, identical or different, can also represent alkoxy, aryloxy or amino groups.

$R_1$ to $R_{11}$ can also be hydrogen or a halogenide.

Two adjacent radicals among the $R_2$-$R_5$ or $R_6$-$R_{11}$ groups can form rings.

Preferably, $R_1$ is a methyl group and $R_{11}$ is hydrogen, b) optionally isolating at least one product resulting from the reaction of A with B, c) stage of oxidation of the mixture of compounds A and B, or of the product isolated in stage b), d) optionally isolating at least one product resulting from stage c), e) adding an activating agent (compound C), and f) optionally adding a solvent (compound D).

The composition thus obtained has a good catalytic activity, notably prolonged activities, particularly at temperatures up to 80° C.-100° C. it also allows to minimize the amount of by-products obtained, in particular to reduce the amount of polymers and waxes in relation to the catalytic compositions known in the prior art.

The present invention also describes an oligomerization, co-dimerization or polymerization method using said catalytic compositions.

Compound A (Metallic Precursor)

The iron compound can be selected from among metal halogenides such as iodides, bromides or chlorides, nitrates, sulfates, amidinates, carboxylates such as acetates, triflates; oxalates, diketonates. Organometallic compounds or hydrides can also be used.

Compound A can be of monomeric, dimeric or oligomeric nature of higher order.

Lewis base adducts of metal compounds can also be used according to the present invention. Examples of Lewis bases that can be used according to the present invention are ethers, amines, thioethers and phosphines.

The iron compound has a valence of 0, I or II.

Examples of type A compounds usable according to the present invention are: $FeCl_2$; $FeCl_2, 4H_2O$; $FeCl_2, 1,5THF$; $FeCl_2, 2$-pyridine; $FeBr_2$; $Fe(NSiMe_3)_2$; $Fe(CH_3COO)_2$; $Fe(C_6H_5N)_2(CH_2SiMe_3)_2$; $Fe(NO_3)_2$; $Fe(CF_3SO_3)_2$; $Fe(N-SiMe_3)_2$; $Fe(2$-ethylhexanoate$)_2$.

Description of the Reaction of X with Y and of the Isolation of a Compound B

Compound B results from the condensation of compounds X and Y, and it comprises at least one pyridine group.

Compound X is a pyridine or a substituted pyridine comprising at least one aldehyde function or a ketone function. The general formula of compound X is given below:

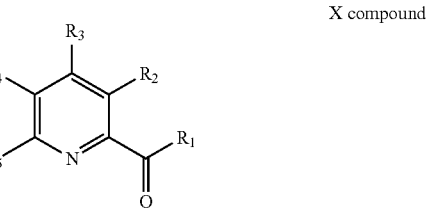

Compound X is, for example, 2-acetylpyridine or 4-methyl-2-acetylpyridine.

Compound Y belongs to the aminoquinoleine family and derivatives thereof. The corresponding general formula is given below:

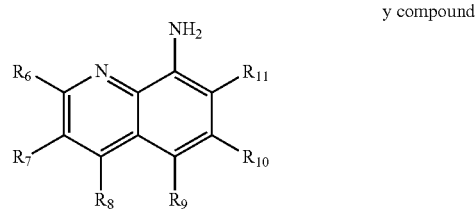

Compound Y is, for example, 8-aminoquinoleine or 2-methyl-8-aminoquinoleine.

The reaction between the two compounds X and Y is preferably carried out in a solvent, at a temperature preferably ranging between 20° C. and 250° C. Compounds X and Y can be introduced in any order.

The solvents used are selected from among conventional organic solvents, polar or apolar, protic or aprotic, such as aromatic or aliphatic hydrocarbons like toluene, xylene, cyclohexane, chlorinated solvents such as dichloromethane, nitro solvents such as acetonitrile, alcohols such as methanol or ethanol. These solvents can be used alone or in admixture. They are preferably dried, by distillation or by passage through an adsorbent, prior to being used.

The reaction of X with Y is preferably carried out in the presence of a catalyst. The catalysts are preferably selected from among Bronsted acids or Lewis acids.

Bronsted acids are of $H^+X^-$ type wherein $X^-$ represents an anion. $X^-$ anions are preferably selected from among the following anions: tetrafluoroborate, tetraalkylborates, hexafluorophosphates, hexafluoroantimonates, alkylsulfonates (for example methylsulfonate), p-toluenesulfonates, perfluorosulfonates (for example trifluoromethylsulfonate), fluorosulfonates, sulfates, phosphates, perfluoroacetates (for example trifluoroacetate), perfluorosulfonamides (for example bis-trifluoromethanesulfonyl amidide of formula $N(CF_3SO_2)_2^-$), fluorosulfonamides, perfluorosulfomethides (for example tris-trifluoromethanesulfonyl methylide of formula $C(CF_3SO_2)_3^-$), carboranes, tetraphenylborates and tetraphenylborate anions whose aromatic rings are substituted.

Lewis acids are, by definition, compounds likely to accept an electron doublet.

Examples thereof are lanthanide triflates, in particular ytterbium triflate $(Yb(OTf)_3)$, scandium triflate.

The reaction between X and Y can optionally be carried out in the presence of iodine.

The reaction between compounds X and Y releases water. The water can be advantageously trapped during the reaction by adding a desiccant such as a molecular sieve. It can also be removed by azeotropic distillation with the reaction solvent.

The ratio between X and Y ranges between 10 and 0.1, preferably between 5 and 0.2.

The main product obtained upon reaction of X with Y can be isolated and purified according to conventional methods used in organic chemistry, such as precipitation, crystallization or liquid chromatography separation on an alumina or silica column.

Compound B preferably contains a phenanthroline-derived motif.

The general formula of compound B is as follows:

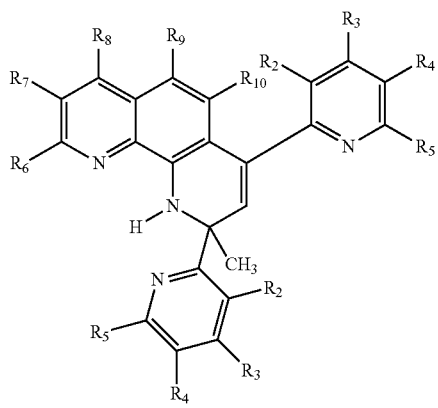

wherein $R_2$ to $R_{10}$, identical or different, are selected from among hydrogen, alkyl groups, saturated or not, cycloalkyl or aromatic, aryl or aralkyl, possibly substituted, alkoxy, aryloxy or amino groups, a halogenide.

Groups $R_2$ to $R_{10}$, identical or different, can also represent organic radicals wherein one or more hydrogen atoms are replaced by halogenides, a fluoride for example, or groups comprising at least one heteroatom such as oxygen, nitrogen, sulfur, phosphorus or silicon. These heteroelements can be contained in saturated or unsaturated or aromatic alkyl rings.

According to the method of the present invention, the molar ratio between compound B and compound A ranges between 1 and 10, preferably between 1 and 2.

Description of Stage a) of Mixing A and B

Mixing A and B can be performed in any order, preferably in a solvent.

Examples of organic solvents that can be used in stage a) according to the present invention are hydrocarbons such as pentane, hexane, cyclohexane or heptane, aromatic hydrocarbons such as benzene, toluene or xylenes, chlorinated solvents such as dichloromethane, protic solvents such as alcohols, or acetone, acetonitrile, diethylether, tetrahydrofuranne dimethylsulfoxide (DMSO) and dimethylformamide (DMF). These solvents can be used alone or in admixture.

The organic solvent is preferably selected so as to dissolve the mixture of A and B.

Description of Stage b) of Isolating at Least One of the Products from Stage a)

Isolating at least one of the products resulting from stage a) can be done by evaporation of the solvent of the reaction of A with B, followed by washing the compounds obtained, or by precipitation or crystallization.

Description of Oxidation Stage c)

Oxidation is preferably carried out by adding, while stirring, the oxidizing agent to the mixture of A and B or to at least one of the products resulting from stage b), preferably in solution in a solvent.

The oxidizing agent used in the present invention is preferably molecular oxygen, air or oxygen-enriched air, or another gas such as an inert gas containing molecular oxygen. Oxygen can also be used dissolved in a liquid. In this case, oxidation is carried out by bubbling the oxidizing agent in the mixture of A and B or at least one of the products from stage b), preferably in solution in a solvent.

One may also consider using as the oxidizing agent an organic compound comprising one or more oxygen atoms in its structure. An example thereof is hydrogen peroxide.

The temperature during oxidation preferably ranges between 10° C. and 100° C.

Examples of the organic solvents that can be used in the oxidation stage according to the present invention are hydrocarbons such as pentane, hexane, cyclohexane or heptane, aromatic hydrocarbons such as benzene, toluene or xylenes, chlorinated solvents such as dichloromethane, protic solvents such as alcohols, or acetone, acetonitrile, diethylether, tetrahydrofuranne (THF), dimethylsulfoxide (DMSO) and dimethylformamide (DMF). These solvents can be used alone or in admixture.

Description of Stage d) of Isolating at Least One Product Resulting from Stage c)

Isolating at least one product from stage c) can be done by evaporation of the solvent of the oxidation stage, followed by washing of the compound(s) obtained, or by precipitation or crystallization.

Description of Stage e) of Adding the Activating Agent (Compound C)

The activating agent (compound C) can be defined as any species capable of forming a metal-carbon or metal-hydrogen bond.

If compound A already contains at least one metal-carbon bond, the activating agent can be a Lewis acid, a Bronsted acid or an alkylating agent, or any compound likely to achieve hydrogenolysis of a metal-carbon bond.

Preferably, the activating agent is selected from among aluminium derivatives such as, for example, aluminoxanes, organo-aluminiums, aluminium halogenides, aluminates, boron derivatives such as, for example, boranes or borates, zinc derivatives such as, for example, organo-zincs.

By way of example, the organo-aluminiums that can be used as activators in the catalytic composition according to the invention are of general formula $AlR_nX'_{(3-n)}$ with n ranging between 1 and 3, groups R, identical or different, being selected from among the alkyl, aryl or aralkyl groups having 1 to 12 carbon atoms and the X', identical or different, being selected from among halogenides, alkoxy, aryloxy, amidides or carboxylates. The organo-aluminiums are preferably selected from the trialkylaluminium group or the dialkylaluminium chloride group or the alkylaluminium dichloride group.

The aluminoxanes that can be used as activators in the catalytic composition are selected from among alkylaluminoxanes such as methylaluminoxane (MAO) or ethylaluminoxane (EAG), or among modified alkylaluminoxanes such as modified methylaluminoxane (MMAO).

According to the method of the present invention, the molar ratio between compound C (activator) and compound A (metal) ranges between 1 and 10 000, preferably between 1 and 1000, and more preferably between 1 and 200.

According to the method of the present invention, the molar ratio between compound C (activator) and at least one product resulting from contacting compound A and compound B ranges between 1 and 10 000, preferably between 1 and 1000, and more preferably between 1 and 200.

Description of Stage f) of Adding the Solvent (D)

The organic solvent used in the catalytic composition is preferably an aprotic solvent. Examples of solvents that can be used, alone or in admixture, in the method according to the present invention are hydrocarbons such as pentane, hexane, cyclohexane or heptane, aromatic hydrocarbons such as benzene, toluene or xylenes, chlorinated solvents such as dichloromethane or chlorobenzene, or acetonitrile, diethylether, tetrahydrofuranne (THF). The organic solvent is preferably a saturated or unsaturated aliphatic solvent or an aromatic hydrocarbon solvent.

Catalytic Oligomerization, Co-Dimerization or Polymerization Method

The catalytic composition prepared according to the method of the present invention is used for olefin dimerization, co-dimerization, oligomerization or polymerization.

The olefins likely to be converted by the catalytic compositions according to the invention are more particularly ethylene, propylene, n-butenes and n-pentenes, alone or in admixture (co-dimerization), pure or diluted by an alkane, as they can be found in "cuts" resulting from petroleum refining processes such as catalytic cracking or steam cracking.

The catalytic olefin conversion reaction can be carried out in a closed system, a semi-open system or under continuous conditions, with one or more reaction stages. Vigorous agitation should provide good contact between the reactant(s) and the catalytic composition.

The reaction temperature can range from −40° C. to +250° C., preferably from 0° C. to +150° C.

The heat generated by the reaction can be eliminated by any means known to the person skilled in the art.

The pressure can range from atmospheric pressure to 20 MPa, preferably from atmospheric pressure to 10 MPa.

EXAMPLES

Reaction of X with Y: Synthesis of Compounds B

Example 1

Synthesis of a Ligand B1

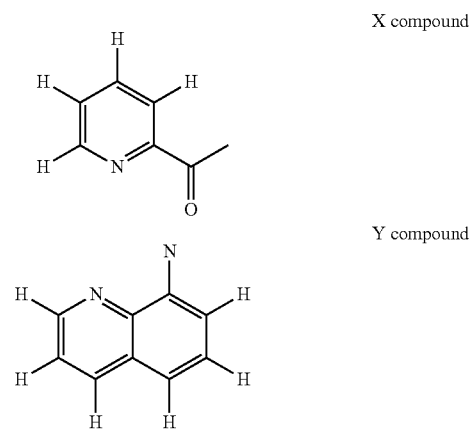

Condensation of 6.89 g of 2-acetylpyridine (56.9 mmol) and of 4.1 g of 8-aminoquinoleine (28.4 mmol) with 1.3 mL formic acid HCOOH is carried out in 75 mL anhydrous MeOH. The reaction medium is stirred under reflux for 72 h. After evaporation of the methanol under vacuum, the ketone is evaporated under vacuum and by heating to 60° C. The raw product obtained is purified by chromatography on an alumina column in order to remove the 8-aminoquinoleine, then on neutral silica (eluent $CH_2Cl_2$/AcOEt 80/20). 2.4 g of a yellowish solid are obtained. The yield obtained is 30%.

Characterizations are performed using $^1H$ and $^{13}C$ NMR analysis methods, IR spectroscopy and GC/MS mass spectroscopy.

$^1H$ NMR: $\delta_H$ (300 MHz, $CD_2Cl_2$) 1.90 (s, 3H), 6.17 (d, 1H, J 2.3 Hz), 6.95 (d, 1H, J 8.6 Hz), 7.00 (s, 1H), 7.11 (ddd, 1H, J 7.3, 4.7 and 1.4 Hz), 7.29 (ddd, 1H, J 7.6, 4.7 and 1.2 Hz), 7.32 (d, 1H, J 8.5 Hz), 7.35 (dd, 1H, J 8.2 and 4.35 Hz), 7.49 (dt, 1H, J 7.9 and 1.1 Hz), 7.59 (dt, 1H, J 7.94 and 1.15 Hz), 7.62 (td, 1H, J 7.5 and 1.9 Hz), 7.76 (td, 1H, J 7.65 and 1.2 Hz), 8.02 (dd, 1H, J 8.3 and 1.8 Hz), 8.60 (dq, 1H, J 4.8 and 0.9 Hz), 8.69 (dq, 1H, J 4.9 and 0.9 Hz), 8.75 (dd, 1H, J 4.2 and 1.7 Hz) ppm;

$^{13}C$ NMR: $\delta_C$ (75 MHz, $CD_2Cl_2$) 31.1, 59.1, 113.8, 115.5, 120.3, 121.8, 121.9, 122.7, 123.9, 125.1, 128.9, 130.0, 136.1, 136.5, 136.8, 136.9, 137.7, 140.6, 148.0, 149.61, 149.64, 158.2, 166.6 ppm;

IR: 3371, 3048, 2968, 1632, 1583, 1563, 1508, 1464, 1428, 1378, 1294, 1225, 1100, 1044, 991, 823, 804, 783, 750 cm$^{-1}$.

GC/MS: 350, 335, 272, 256, 167.

The analyses performed allow to propose the following structure for compound B1:

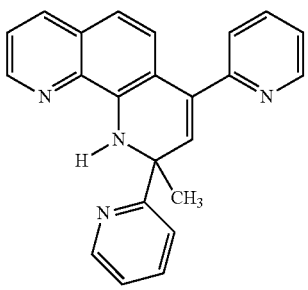 [SMILES: CC1(c2ccccn2)C=C(c2ccccn2)c2ccc3cccnc3c2N1]

Example 2

Synthesis of a Ligand B2

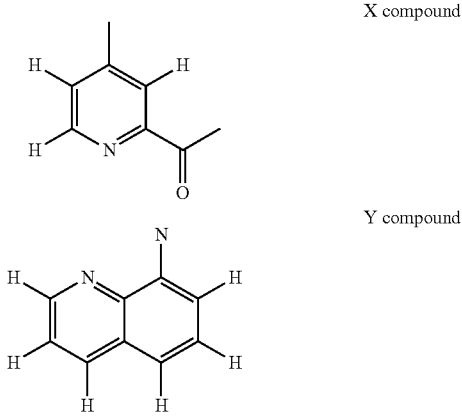

Synthesis is achieved as in Example 1, except that 4.00 g of 4-methyl-2-acetylpyridine (29.6 mmol) and 4.27 g of 8-aminoquinoleine (29.6 mmol) are used.

This mixture is brought into solution in 60 mL distilled MeOH with 0.8 mL formic acid, then heated under reflux for 96 hours.

1.8 g of a bright yellow solid is obtained, which corresponds to a 32% yield.

The solid is characterized by $^1$H NMR, $^{13}$C NMR, IR and mass spectroscopy.

$^1$H NMR: $\delta_H$ (300 MHz, CD$_2$Cl$_2$) 1.85 (s, 3H), 2.28 (s, 3H), 2.40 (s, 3H), 6.10 (d, 1H, J 2.3 Hz), 6.93 (d, 1H, J 8.6 Hz), 6.96 (m, 1H), 7.12 (dm, 1H, J 5.0 Hz), 7.30-7.40 (m, 4H), 8.01 (dd, 1H, J 8.4 and 1.4 Hz), 8.44 (d, 1H, J 4.9 Hz), 8.52 (d, 1H, J 5.1 Hz), 8.74 (dd, 1H, J 4.2 and 1.7 Hz) ppm;

$^{13}$C NMR: $\delta_C$ (75 MHz, CD$_2$Cl$_2$) 21.2, 21.4, 31.2, 59.1, 113.7, 115.4, 121.2, 121.8, 122.9, 123.7, 124.7, 125.3, 128.9, 129.6, 136.1, 136.4, 137.8, 140.6, 147.9, 148.1, 148.2, 149.31, 149.32, 158.2, 166.4 ppm;

IR: 3359, 2974, 2921, 2822, 1640, 1599, 1555, 1509, 1467, 1448, 1423, 1378, 1350, 1116, 1090, 1031, 991, 847, 827, 803, 779, 711, 696 cm$^{-1}$.

MS: EI m/z 363, 286, 270, 256, 243, 189, 181.

The analyses performed allow to propose the following structure for compound B2:

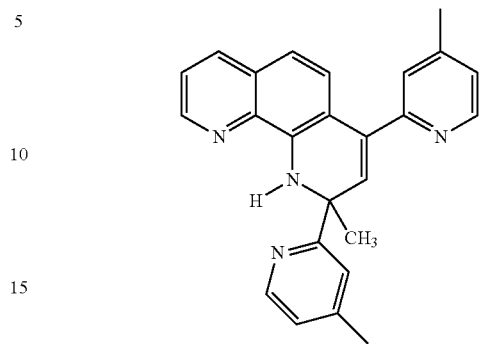

Products Obtained after Contacting Compounds A and B (Stage a))

Example 3

Synthesis Achieved from Ligand B1 and an Iron Chloride

Ligand B1 described in Example 1 (1.297 g, i.e. 3.7 mmol) and FeCl$_2$, 4H$_2$O (0.736 g, i.e. 3.7 mmol) are dissolved in 30 mL anhydrous THF. The dark purple reaction medium is stirred for 12 h under argon at ambient temperature. A pink-purple precipitate appears. 7 mL heptane are added, then the medium is filtered by means of a cannula. The pink-purple solid is washed with Et$_2$O (3×10 mL), then dried under vacuum. 1.742 g of a pink powder is obtained (yield: 99%).

IR: 3144, 2974, 2868, 1602, 1583, 1568, 1500, 1475, 1459, 1432, 1363, 1124, 1059, 1012, 911, 849, 786, 772, 759, 748, 713, 688, 641, 595 cm$^{-1}$.

Elemental analysis for C$_{23}$H$_{18}$Cl$_2$FeN$_4$ C, 58.65; H, 11.12; N, 4.28%.

Exact mass measured: 476.02563.

UV: in CH$_2$Cl$_2$: 245, 267, 333 and 454 nm.

Mössbauer spectroscopy analysis was carried out and the spectrum of the complex obtained shows a high-spin divalent major iron compound.

Example 4

Synthesis Achieved from Ligand B2 and an Iron Chloride

The complexation of ligand B2 described in Example 2 is carried out in the same way as in Example 3.

IR: 3059, 2970, 2866, 1614, 1600, 1557, 1505, 1444, 1368, 1125, 1055, 900, 842, 835, 815, 798, 786, 461 cm$^{-1}$.

Exact mass measured: 504.0558 g.

Example 5

Synthesis from Ligand B1 and an Iron Bromide

The complexation of ligand B1 described in Example 1 is carried out as in Example 3, but with anhydrous FeBr$_2$. 506 mg of a pink-purple powder are obtained (yield: 89%).

IR: 3144, 3063, 2972, 2868, 1602, 1584, 1557, 1500, 1474, 1460, 1430, 1372, 1117, 1059, 1012, 910, 847, 783, 771, 747, 688, 641 cm$^{-1}$.

Example 6

Oxidation of the Complex Obtained in Example 3

The iron complex described in Example 3 (0.200 g) is dissolved in 100 mL previously degassed acetonitrile $CH_3CN$. An $O_2$ stream is passed over the reaction medium for 15 min. The colour of the complex changes from pink to dark purple. The mixture is stirred for one night at ambient temperature under an $O_2$ atmosphere. The reaction medium is then concentrated under vacuum and 20 mL $Et_2O$ are added. The product precipitates. The solid is filtered by means of a cannula, then washed with $Et_2O$ (3×10 mL). A black powder is obtained 0.210 g).

IR: 3061, 2967, 1603, 1585, 1566, 1494, 1454, 1396, 1374, 1107, 1051, 1020, 864, 818, 778, 748, 653 $cm^{-1}$.

El. Anal. C, 54.36; H, 3.36; N, 10.61%.

UV: $1.10^{-4}$M in $CH_2Cl_2$: 230.5; 257.5; 291; 381; 554; 804 nm.

The Mössbauer spectrum of the sample containing the complex obtained mainly shows the existence of a high-spin Fe(III) compound.

Example 7

Oxidation of the Complex Obtained in Example 4

Oxidation of the product obtained in Example 4 is carried out as in Example 6. The oxidized complex comes in form of a black powder.

IR: 3355, 3049, 2970, 2921, 1663, 1615, 1602, 1558, 1497, 1455, 1392, 1100, 1020, 819, 798, 696 $cm^{-1}$.

Example 8

Oxidation of the Complex Obtained in Example 5

Oxidation of the product obtained in Example 5 is carried out as in Example 6. The oxidized complex comes in form of a black powder.

IR: 3059, 2968, 1668, 1602, 1585, 1566, 1495, 1455, 1393, 1107, 1049, 1019, 992, 820, 776, 749 $cm^{-1}$.

Example 9

Catalytic Tests

The catalytic test is carried out in a 250-mL Grignard type reactor provided with a double jacket and a bar magnet. Before the reaction, the reactor is placed under vacuum (approximately $6.10^{-2}$ mbar) and heated to 90° C. for 4 h. After cooling down to ambient temperature, the reactor is pressurized to 3.5 MPa ethylene (0.5 MPa above the planned test pressure) so as to test its tightness throughout one night. The reactor is then heated to 80° C. 42.4 mL distilled toluene, then the MAO solution in toluene (10% in toluene, 200 eq, 2.6 mL), then the catalytic solution ($2.10^{-5}$ moles catalyst in 5 mL toluene) are fed into the reactor under 0.05 MPa ethylene.

The reactor is placed under 3 MPa ethylene pressure. The ethylene pressure is kept constant during the test, the ethylene inflow being controlled by a pressure regulator connected to a ballast placed on a balance. The catalyst activity corresponds to the ethylene consumption measured by the loss of weight of the ballast connected to the reactor and containing the ethylene. The ethylene consumption is measured as a function of time (see curves in the figures). It gives an indication of the catalyst stability over time.

At the end of the reaction, the reactor is depressurized. The gas volume is measured by a gas meter and analyzed. The liquid phase is withdrawn, weighed, and the catalyst is neutralized by adding ethanol. After trap-to-trap vacuum distillation, the liquid phase is analyzed by gas chromatography. A complete balance is performed (material entering, material leaving).

| Complex | Productivity g/g Fe | $C_4$ % weight | % α | $C_6$ % weight | % α | $C_8$ % weight | % α | $C_{10}$ % weight | % α | $C_{12}$ % weight | % α | PE + waxes |
|---|---|---|---|---|---|---|---|---|---|---|---|---|
| complex described in Example 6 | 14050 | 51.4 | 93.9 | 23.8 | 83.6 | 9.8 | 83.8 | 3.1 | 82.4 | 0.6 | — | 11.2 |

Al/Fe: 200 eq, Fe: $2.10^{-5}$ mol, toluene 50 mL, P: 30 bar, T: 80° C., test duration: 60 min, MAO: Aldrich, 10% in toluene

| Complex | Productivity g/g Fe | $C_4$ % weight | % α | $C_6$ % weight | % α | $C_8$ % weight | % α | $C_{10}$ % weight | % α | $C_{12}$ % weight | % α | PE + waxes |
|---|---|---|---|---|---|---|---|---|---|---|---|---|
| complex described in Example 7 | 12044 | 40.7 | 97 | 21.7 | 83.8 | 9.4 | 86.0 | 2.1 | 81.8 | 0.3 | — | 25.8 |

Al/Fe: 200 eq, Fe: $2.10^{-5}$ mol, toluene 50 mL, P: 30 bar, T: 80° C., test duration: 60 min, MAO: Albemarle, 9,2% in toluene

| Complex | Productivity g/g Fe | $C_4$ % weight | % α | $C_6$ % weight | % α | $C_8$ % weight | % α | $C_{10}$ % weight | % α | $C_{12}$ % weight | % α | PE + waxes |
|---|---|---|---|---|---|---|---|---|---|---|---|---|
| complex described in Example 8 | 14194 | 44.1 | 95.5 | 21.3 | 84.3 | 7.9 | 84.7 | 2.3 | 80.3 | 0.6 | — | 23.9 |

Al/Fe: 200 eq, Fe: $2.10^{-5}$ mol, toluene 50 mL, P: 30 bar, T: 80° C., test duration: 60 min, MAO: Aldrich, 10% in toluene

Example 10

Comparative

The catalytic test is carried out under the same conditions as in Example 9, except that the complex used is the bis-imino-pyridine complex described below. The complex is used without any oxidation stage.

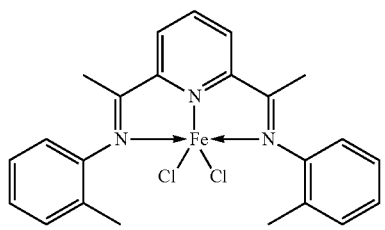

Figure 4:
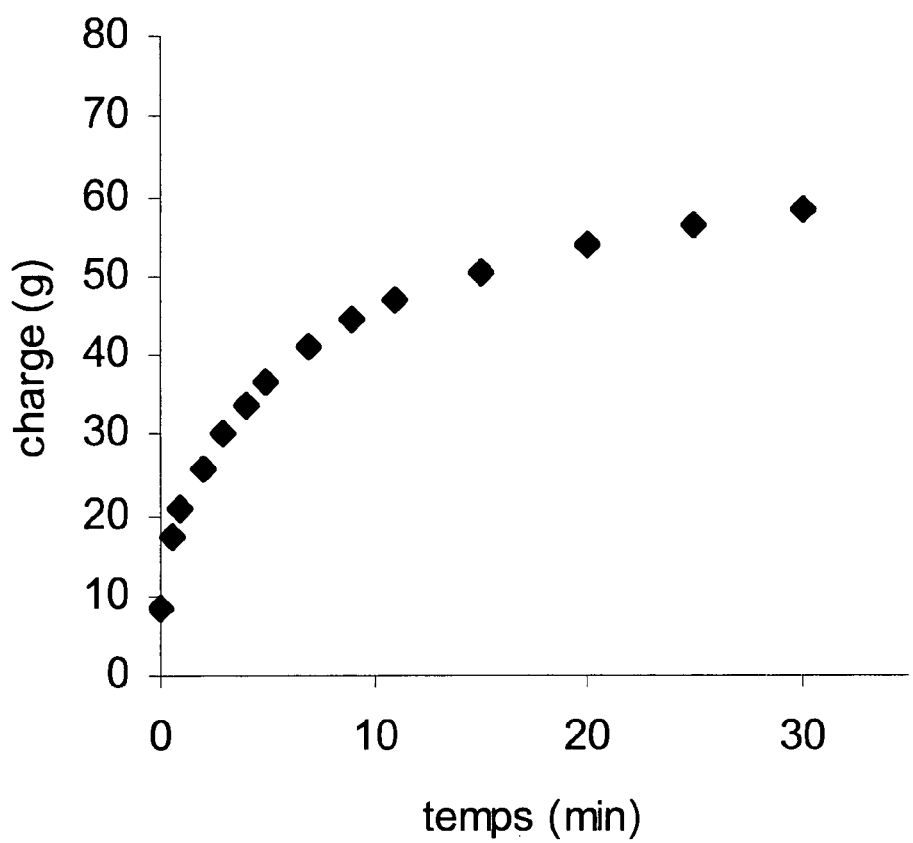

It can be observed that the mass of polymer produced is very large: 69% of the products formed. Besides, the curve describing the mass of ethylene consumed as a function of time (FIG. 4) shows that, after the first 10 minutes, the system deactivates very rapidly.

The invention claimed is:

1. A method of preparing a catalytic composition comprising the following stages:
   a) contacting, optionally in the presence of a solvent, at least one iron compound (compound A) with at least one compound B resulting from the condensation of a compound X with a compound Y whose general formulas are given below:

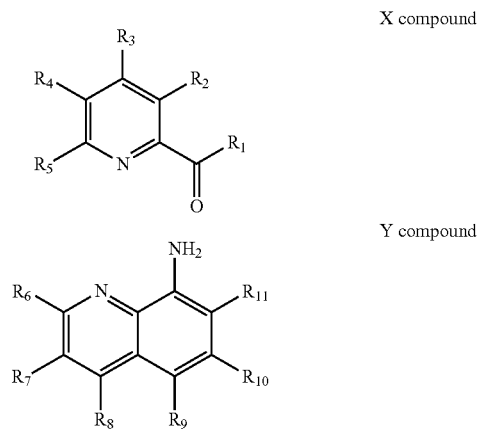

X compound

Y compound $R_1$ to $R_{11}$, identical or different, representing alkyl groups, saturated or not, cycloalkyl or aromatic, aryl or aralkyl, optionally substituted, hydrogen, a halogenide, alkoxy, aryloxy or amino groups,
   b) optionally isolating at least one product resulting from the reaction of A with B,
   c) oxidizing with an oxidizing agent of the resultant mixture of compounds A and B, or of the product optionally isolated in stage b),
   d) optionally isolating at least one product resulting from stage c),
   e) adding an activating agent (compound C), and
   f) optionally adding a solvent (compound D).

2. A method as claimed in claim 1, wherein $R_1$ to $R_{11}$, identical or different, represent hydrocarbyl radicals wherein one or more hydrogen atoms are replaced by halogenides, or groups comprising at least one of oxygen, nitrogen, sulfur, phosphorus or silicon optionally contained in saturated or unsaturated or aromatic alkyl rings.

3. A method as claimed in claim 1, wherein $R_1$ is a methyl group and $R_{11}$ is hydrogen.

4. A method as claimed in claim 1, wherein said iron compound (compound A) is selected from metal halogenides, nitrates, sulfates, amidides, carboxylates, oxalates, diketonates, organometallic compounds or hydrides.

5. A method as claimed in claim 1, wherein the iron compound is an adduct with a Lewis base.

6. A method as claimed in claim 1, wherein compound B and compound A are provided in a molar ratio range of between 1:1 and 10:1.

7. A method as claimed in claim 1, wherein said contacting compounds A and B (stage a) is carried out in an organic solvent selected from among saturated hydrocarbons, aromatic hydrocarbons, chlorinated organic solvents, or protic solvents, alone or in admixture.

8. A method as claimed in claim 1, comprising in stage b) isolating at least one product from stage a) by evaporation of the solvent introduced in stage a), or by precipitation or crystallization.

9. A method as claimed in claim 1, wherein the oxidizing agent in stage c) is molecular oxygen, air or oxygen-enriched air, or a gas containing molecular oxygen, or oxygen dissolved in a liquid.

10. A method as claimed in claim 1, wherein the oxidizing agent in stage c) is an organic compound comprising one or more oxygen atoms in the structure thereof.

11. A method as claimed in claim 1, wherein the oxidation in stage c) is carried out in a solvent.

12. A method as claimed in claim 11, wherein the solvent is selected from saturated hydrocarbons, aromatic hydrocarbons, chlorinated solvents, or protic solvents.

13. A method as claimed in claim 1, wherein oxidation in stage (c) is carried out by bubbling, while stirring, dry gaseous oxygen in a liquid mixture of A and B or of at least one of the products resulting from stage b).

14. A method as claimed in claim 1, wherein the temperature during oxidation in stage (c) ranges between 10° C. and 100° C.

15. A method as claimed in claim 1, comprising stage d) wherein at least one of the products resulting from stage c) is isolated by evaporation of the solvent, by precipitation or crystallization.

16. A method as claimed in claim 1, wherein the activating agent introduced in stage e) is a Lewis acid, a Bronsted acid, or an alkylating agent compound capable of hydrogenolysis of a metal-carbon bond (M-C).

17. A method as claimed in claim 16, wherein the activating agent is selected from aluminoxanes, organo-aluminiums, aluminium halogenides, aluminates, boranes, borates, organo-zincs, methylaluminoxane (MAO), ethylaluminoxane (EAO) or modified methylaluminoxane (MMAO).

18. A method as claimed in claim 17, wherein the molar ratio between the activating agent (compound C) and the iron compound (compound A) ranges between 1 and 10 000.

19. A method as claimed in claim 1, wherein the molar ratio between the activating agent (compound C) and at least one product resulting from contacting compounds A and B ranges between 1 and 10 000.

20. A method as claimed in claim 1, comprising stage (f), wherein the solvent added in stage f) is selected from saturated hydrocarbons, aromatic hydrocarbons, or protic solvents.

21. A catalytic composition prepared according to the method as claimed in claim 1.

22. In a catalytic olefin dimerization, co-dimerization, oligomerization or polymerization method the improvement wherein the catalyst is comprises the catalytic composition according to claim 21.

* * * * *

UNITED STATES PATENT AND TRADEMARK OFFICE
CERTIFICATE OF CORRECTION

PATENT NO. : 8,575,056 B2
APPLICATION NO. : 12/811635
DATED : November 5, 2013
INVENTOR(S) : Claudine Rangheard et al.

It is certified that error appears in the above-identified patent and that said Letters Patent is hereby corrected as shown below:

In the Claims:

Column 13, line 61 (Claim 1), reads as follows: -- c) oxidizing with an oxidizing agent of the resultant mix- -- Should read: -- c) oxidizing with an oxidizing agent the resultant mix- --

Column 14, line 10 (Claim 4), reads as follows: -- compound (compound A) is selected from metal halogenides, -- Should read: -- compound (compound A) is metal halogenides, --

Column 14, line 35 (Claim 11), reads as follows: -- 11. A method as claimed in claim 1, wherein the oxidation -- Should read: -- 11. A method as claimed in claim 1, wherein oxidation --

Column 14, line 38 (Claim 12), reads as follows: -- selected from saturated hydrocarbons, aromatic hydrocar- -- Should read: -- saturated hydrocarbons, aromatic hydrocar- --

Column 15, line 9 (Claim 22), reads as follows: -- wherein the catalyst is comprises the catalytic composition -- Should read: -- wherein the catalyst comprises the catalytic composition --

Signed and Sealed this
First Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,575,056 B2                                                                 Page 1 of 1
APPLICATION NO.    : 12/811635
DATED              : November 5, 2013
INVENTOR(S)        : Rangheard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 556 days.

Signed and Sealed this
Twenty-second Day of September, 2015

Michelle K. Lee
*Director of the United States Patent and Trademark Office*